(12) United States Patent
Toida (10) Patent No.: US 6,618,152 B2
(45) Date of Patent: Sep. 9, 2003

(54) OPTICAL COHERENCE TOMOGRAPHY APPARATUS USING OPTICAL-WAVEGUIDE STRUCTURE WHICH REDUCES PULSE WIDTH OF LOW-COHERENCE LIGHT

(75) Inventor: Masahiro Toida, Kaisei-machi (JP)

(73) Assignee: Fuji Photo Film Co., Ltd., Kanagawa-Ken (JP)

(*) Notice: Subject to any disclaimer, the term of this patent is extended or adjusted under 35 U.S.C. 154(b) by 0 days.

(21) Appl. No.: 09/849,294

(22) Filed: May 7, 2001

(65) Prior Publication Data

US 2001/0043332 A1 Nov. 22, 2001

(30) Foreign Application Priority Data

May 9, 2000 (JP) ........................ 2000/135404

(51) Int. Cl.[7] ................................................ G01B 9/02
(52) U.S. Cl. ........................................ 356/479; 356/497
(58) Field of Search .................................. 356/479, 497

(56) References Cited

U.S. PATENT DOCUMENTS

| | | | |
|---|---|---|---|
| 5,469,261 A | * 11/1995 | Hellmuth et al. | 356/479 |
| 5,760,901 A | * 6/1998 | Hill | 356/479 |
| 5,975,697 A | 11/1999 | Podoleanu et al. | 351/206 |
| 6,163,638 A | * 12/2000 | Eggleton et al. | 385/37 |
| 6,195,484 B1 | * 2/2001 | Brennan, III et al. | 385/37 |

FOREIGN PATENT DOCUMENTS

| | | | |
|---|---|---|---|
| DE | 199 04 565 A1 | 9/1999 | G02F/1/39 |
| EP | 0 998 067 A2 | 5/2000 | H04B/10/18 |
| GB | 2 316 760 A | 8/1996 | G02B/6/00 |
| WO | 01/22539 A1 | 3/2001 | G02B/27/09 |

OTHER PUBLICATIONS

B.E. Bouma, et al.; "Self–phase–modulated Kerr–lens mode–locked Cr:forsterite laser source for optical coherence tomography" Nov. 15, 1996; vol. 21.; No. 22; Optics Letters.

"Self–phase–modulated Kerr–lens mode–locked Cr:Forsterite laser source for optical coherence tomography" Nov. 15, 1996/vol. 21, No.22/OPTICS LETTERS.

* cited by examiner

Primary Examiner—Stephone B Allen
(74) Attorney, Agent, or Firm—Sughrue Mion, PLLC (57) ABSTRACT

In an optical coherence tomography apparatus: low-coherence light from a light source is split into signal light and reference light; at least one of the frequencies of the signal light and the reference light is shifted so as to produce a predetermined frequency difference between the frequencies; the reference light and a portion of the signal light reflected from the object are optically multiplexed so as to produce interference light; and the optical intensity of the interference light is detected in order to obtain a tomographic image of the object. In the light source, the pulse width of pulsed light emitted from a pulsed light source unit is reduced by an optical-waveguide structure. The optical-waveguide structure is made of a material having a normal dispersion characteristic, and includes a structure which realizes an anomalous dispersion characteristic so as to reduce the pulse width of the pulsed light.

18 Claims, 4 Drawing Sheets

OPTICAL COHERENCE TOMOGRAPHY APPARATUS USING OPTICAL-WAVEGUIDE STRUCTURE WHICH REDUCES PULSE WIDTH OF LOW-COHERENCE LIGHT

BACKGROUND OF THE INVENTION

1. Field of the Invention

The present invention relates to an optical coherence tomography apparatus which irradiates an object with low-coherence light as signal light, and acquires a tomographic image of the object, where the tomographic image represents information on fine structures on and under a surface of the object, based on the signal light which is reflected from the surface and subsurface portions of the object.

2. Description of the Related Art

Conventionally, optical coherence tomography apparatuses using low-coherence light are used. In particular, optical coherence tomography apparatuses in which intensities of low-coherence interference light are detected by heterodyne detection are used for obtaining a tomographic image of subretinal fine structures or the like.

In the above optical coherence tomography apparatuses, low-coherence light emitted from a light source such as a superluminescent diode (SLD) is split into signal light and reference light, and the frequency of the reference light is slightly shifted by using a piezo electric element or the like. Next, an object is irradiated with the signal light, and the reference light and reflected light from a predetermined depth in the object are optically multiplexed so as to produce interference light. Then, the intensity of the reflected light is detected by heterodyne detection based on interference light in order to obtain tomographic information. In this detection, information on a deep portion of the object, to which the round trip optical length of the signal light coincides with the optical length of the reference light, is obtained. In addition, when the optical length of the reference light is varied by moving a movable mirror or the like which is arranged in an optical path of the reference light, information on another area of the object located at a different depth can be obtained.

In the above optical coherence tomography apparatuses, it is desirable that the interference between the reference light and the signal light occurs only when the lengths of the optical paths of the reference light and the signal light precisely coincide. However, in practice, the interference between the reference light and the signal light occurs when the difference between the lengths of the optical paths of the reference light and the signal light is equal to or less than the coherence length of the light source, the interference occurs. That is, the resolution in the low-coherence interference is determined by the coherence length of the light source.

Generally, the coherence length is dependent on the type of the light source, the oscillation mode, noise, and the like. Usually, when laser light is used as the above low-coherence light, it is possible to regard the coherence length as being approximately proportional to the pulse width.

For example, when a pulse laser which emits pulsed laser light having a center wavelength of 800 nm and a pulse width of 25 fs (i.e., $25 \times 10^{-15}$ sec) is used, the coherence length is about 14 micrometers. In addition, when an SLD which emits pulsed light having a center wavelength of 800 nm and a spectral width of 20 nm is used, the coherence length is also about 14 micrometers. That is, when these are used as the light sources in the above optical coherence tomography apparatuses, the resolution is about 14 micrometers. Therefore, when the object includes a plurality of layers within a thickness equal to the coherence length, it is not possible to distinguish the respective layers based on the reflected light.

In addition, recently, in the field of clinical medicine, usefulness of the tomographic image of living tissue is widely known. For example, demands for high-resolution tomographic images of living tissue which scatters light more highly than eyeballs are growing. In order to satisfy the above demands, a light source which can emit low-coherence light having a low coherence length and high output power is necessary. However, it is impossible to increase the output power of the SLD. In addition, it is also impossible to reduce the pulse width and the coherence length of the SLD since the pulse width of the SLD is determined by its bandgap.

In order to solve the above problem, for example, B. E. Bouma et al., ("Self-phase-modulated Kerr-lens mode-locked Cr:forsterite laser source for optical coherence tomography," Optics Letters Vol. 21, Issue 22, pp.1839–1841, November 1996) propose an apparatus which can obtain a high-resolution tomographic image by using low-coherence light having a short pulse width and high output power. The apparatus includes as a light source a KLM (Kerr-lens mode-locked) Ti:sapphire laser which emits an ultrashort-pulsed light having a pulse width of a few femtoseconds. In this apparatus, low-coherence light having a short pulse width and high output power is obtained by using the above ultrashort-pulsed light, and used as signal light and reference light in order to obtain a high-resolution tomographic image.

However, in the above apparatus, the light source including the KLM (Kerr-lens mode-locked) Ti:sapphire laser is bulky, expensive, and uneasy to handle. That is, in practice, the above apparatus using the KLM (Kerr-lens mode-locked) Ti:sapphire laser is not practicable due to its large size, high cost, and poor usability.

SUMMARY OF THE INVENTION

The object of the present invention is to provide an optical coherence tomography apparatus which uses a small-sized, inexpensive, and easy-to-handle light source, and can acquire a high-resolution tomographic image by using low-coherence interference.

According to the present invention, there is provided an optical coherence tomography apparatus comprising: a light source which emits low-coherence light; an optical splitting unit which splits the low-coherence light into signal light having a first frequency and first reference light having a second frequency; a frequency shifting unit which shifts at least one of the first and second frequencies so that a predetermined frequency difference is produced between the first and second frequencies; an irradiating unit which irradiates an object with the signal light; an optical multiplexing unit which optically multiplexes the reference light and a portion of the signal light which is reflected from a predetermined depth in the object, so as to produce interference light; an image detection unit which detects an optical intensity of the interference light, and obtains a tomographic image of the object based on the optical intensity. The light source comprises a pulsed light source unit which emits pulsed light having a third frequency and a pulse width, and an optical-waveguide structure is made of a material having a normal dispersion characteristic with respect to light which has the third frequency, and includes a structure which realizes an anomalous dispersion characteristic with respect to light which has the third frequency, so as to reduce the pulse width of the pulsed light.

Thus, in the optical coherence tomography apparatus according to the present invention, the pulsed light which has the reduced pulse width is emitted as low-coherence light from the light source.

Specifically, the above predetermined frequency difference is such that a beat signal having a frequency which is equal to the predetermined frequency difference is included in the interference light. The above intensity of the interference light is the intensity of the beat signal. For example, the image detection unit detects the intensity of the beat signal by the heterodyne interferometry or the like.

Generally, the reciprocal of the pulse width of the pulsed laser light emitted from a pulse laser is approximately proportional to the spectral width of the pulsed laser light. That is, when the pulse width is reduced, the spectral width increases, and therefore the coherence length is reduced. Therefore, when the pulse width of the low-coherence light emitted from the light source is reduced, the resolution of the tomographic image can be increased corresponding to the reduction in the coherence length.

In the optical coherence tomography apparatus according to the present invention, the pulse width of the pulsed laser light emitted from the pulsed light source is reduced by the optical-waveguide structure, and the optical-waveguide structure is made of a material having a normal dispersion characteristic with respect to light which has the frequency of the pulsed laser light, and includes a structure which realizes an anomalous dispersion characteristic with respect to the light which has the frequency of the pulsed laser light. That is, low-coherence light having a short coherence length can be obtained by the provision of a small-sized, inexpensive, easy-to-handle light source. In other words, a bulky, expensive, uneasy-to-handle light source, which is required in the conventional optical coherence tomography apparatus, is unnecessary. Thus, the resolution in the low-coherence interference can be improved.

Preferably, the optical coherence tomography apparatus according to the present invention may also have one or any possible combination of the following additional features (i) to (xviii).

(i) The optical-waveguide structure may be a transparent-type finely-structured optical waveguide, a reflection-type Bragg grating, or the like.

(ii) The optical-waveguide structure may comprise at least one Bragg grating formed with a plurality of light-reflecting portions arranged in a longitudinal direction of the optical-waveguide structure at a pitch which varies progressively.

The plurality of light-reflecting portions can be formed by any method. For example, the plurality of light-reflecting portions can be realized by periodically forming projections and depressions in an optical waveguide by etching, or forming cladding having a periodic variation, or periodically forming high-refractive-index portions.

When the optical-waveguide structure is realized by at least one Bragg grating formed with a plurality of light-reflecting portions arranged in a longitudinal direction of the optical-waveguide structure at a pitch which varies progressively, the pitch (or period) of the Bragg grating can be arranged corresponding to the frequency and the pulse width of the pulsed (laser) light emitted from the pulsed light source (e.g., a pulse laser), so that the Bragg grating can efficiently reduce the pulse width of the pulsed (laser) light. In addition, since it is easy to arrange the Bragg grating in the optical path of the pulsed laser light, the light source can be easily manufactured. Even when the pulse width cannot be sufficiently reduced to a desired amount by a Bragg grating, the pulse width can be reduced to the desired amount by arranging a plurality of Bragg gratings in a plurality of stages.

(iii) In the optical coherence tomography apparatus having the feature (ii), the at least one Bragg grating may be at least one frequency-modulation type Bragg grating formed with a plurality of high-refractive-index portions arranged in the longitudinal direction of the optical-waveguide structure at the above-mentioned pitch. In this case, it is easy to form a Bragg grating having a desirable pitch. Therefore, the pulse width can be reduced with high accuracy.

The above frequency-modulation type Bragg grating may be a planar-waveguide type Bragg grating, a fiber Bragg grating, or the like. That is, the above frequency-modulation type Bragg grating may be any Bragg grating which is produced by forming high-refractive-index portions in an optical waveguide at a pitch which varies progressively. Since the fiber grating is easy to place in narrow space, the use of the fiber grating contributes to downsizing of the entire apparatus.

(iv) In the optical coherence tomography apparatus having the feature (ii), the at least one Bragg grating may be at least one linear Bragg grating in which the pitch varies linearly. Since the linear Bragg grating can be easily formed at low cost. Therefore, the cost of the light source can be further reduced.

(v) In the optical coherence tomography apparatus having the feature (ii), the at least one Bragg grating may be at least one chirped fiber Bragg grating.

(vi) The pulsed light source may comprise a fiber laser doped with a rare-earth ion. In this case, it is possible to obtain pulsed laser light having a narrow pulse width and high output power in a desired wavelength band.

(vii) In the optical coherence tomography apparatus having the feature (vi), the pulsed light source may further comprise a second harmonic generator. In this case, it is possible to obtain pulsed laser light in a wavelength band which cannot be obtained from the rare-earth-ion-doped fiber laser per se.

(viii) In the optical coherence tomography apparatus having the feature (vi), the rare-earth ion may be erbium. In this case, pulsed laser light having a narrow pulse width and high output power can be obtained at low cost.

(ix) In the optical coherence tomography apparatus having the feature (vi), the rare-earth ion may be ytterbium. In this case, pulsed laser light having a narrow pulse width and high output power can be obtained at low cost.

(x) The pulsed light source may comprise a titanium sapphire laser. The oscillation wavelength of the titanium sapphire laser is tunable. Therefore, when the titanium sapphire laser is used as the pulsed light source, users can select a desired wavelength band.

(xi) The pulse width of the pulsed light may be in a range from 10 fs to 1 ps. In this case, the pulse width can be efficiently reduced to a desired amount.

(xii) The optical coherence tomography apparatus according to the present invention may further comprise an optical amplifying unit which optically amplifies the reflection light (i.e., the above-mentioned portion of the signal light which is reflected from a predetermined depth in the object) before the reflection light is optically multiplexed with the reference light. It is easy to arrange an optical amplifying unit in the optical path of the reflection light.

(xiii) In the optical coherence tomography apparatus having the feature (xii), the optical amplifying unit may be an optical amplifier comprising an optical waveguide.

(xiv) In the optical coherence tomography apparatus having the feature (xiii), the optical amplifier may be a semiconductor optical amplifier, a Raman amplifier using the stimulated Raman effect, or an optical fiber amplifier. When the optical fiber amplifier is used, it is possible to increase the length of the optical fiber to a length which realizes a desired gain without substantially increasing the size of the optical fiber amplifier, since the optical fiber can be wound for compact placement. Therefore, the reflection light can be amplified with a great gain by using a small-sized optical fiber amplifier unit. Further, since optical fiber amplifiers have low-noise characteristics, it is possible to accurately amplify very weak reflection light.

(xv) In the optical coherence tomography apparatus having the feature (xiv), the optical fiber amplifier may comprise an optical fiber doped with at least one ion from among transition-metal ions, rare-earth ions, and complex ions. In this case, the optical fiber amplifier can achieve a great gain in a desired wavelength band which reflection light belongs to.

(xvi) In the optical coherence tomography apparatus having the feature (xv), the optical fiber may be doped with at least one ion from among transition-metal ions $Ti^{4+}$, $Cr^{3+}$, $Mn^{4+}$, $Mn^{2+}$, and $Fe^{3+}$, rare-earth ions $Sc^{3+}$, $Y^{3+}$, $La^{3+}$, $Ce^{3+}$, $Pr^{3+}$, $Nd^{3+}$, $Pm^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, and $Lu^{3+}$, and complex ions $WO_4^{2-}$, $MoO_4^{2-}$, $VO_4^{3+}$, $Pt(CN)_4^{2-}$, and $WO_6^{6-}$. In addition, since optical fibers can be easily doped with each of these ions, the manufacturing cost of the optical fiber amplifier can be reduced.

(xvii) In the optical coherence tomography apparatus having the feature (xiv), the optical fiber amplifier may comprise a dye-doped optical fiber. In this case, the optical fiber amplifier can achieve a great gain in a desired wavelength band which reflection light belongs to.

(xviii) The object may be a portion of living tissue, and the low-coherence light may have a wavelength in a range from 600 nm to 1,700 nm. In this case, the signal light exhibits desirable transmitting and scattering characteristics in the living tissue, and therefore a desirable tomographic image can be obtained.

DESCRIPTION OF PREFERRED EMBODIMENTS

Embodiments of the present invention are explained in detail below with reference to drawings.

Construction of First Embodiment

Figure 1:
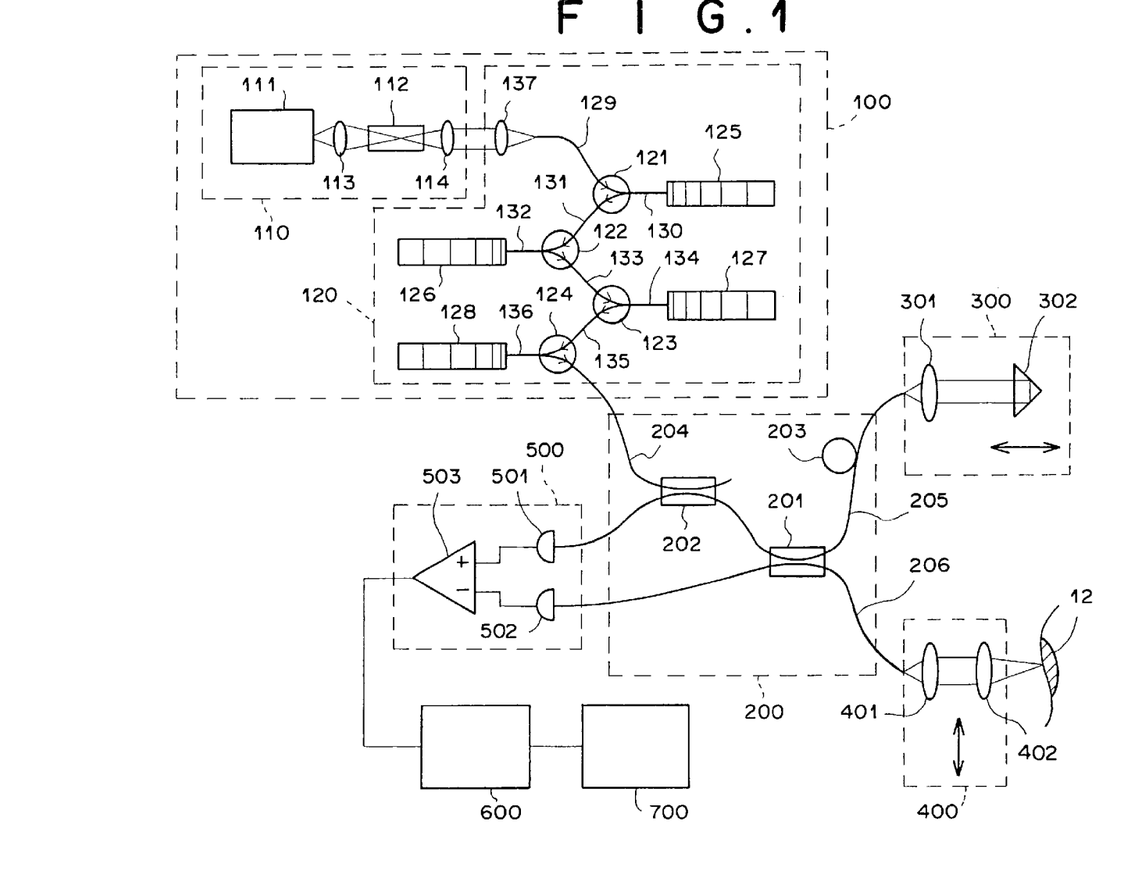
FIG. 1 is a diagram illustrating the construction of the first embodiment of the optical coherence tomography apparatus according to the present invention.

FIG. 1 is a diagram illustrating the construction of the first embodiment of the optical coherence tomography apparatus according to the present invention. The optical coherence tomography apparatus of FIG. 1 comprises a light source unit 100, a fiber-coupling optical system 200, an optical-path delay unit 300, an optical scanning unit 400, a balance-difference detection unit 500, a signal processing unit 600, and an image display unit 700.

The light source unit 100 emits low-coherence light L1 having a center wavelength of 780 nm and a pulse width of about 100 fs. The fiber-coupling optical system 200 functions as an optical splitter and an optical multiplexer. That is, the fiber-coupling optical system 200 splits the low-coherence light L1 emitted from the light source unit 100, into signal light L3 and reference light L2, and optically multiplexes reflection light L4 and the reference light L2 in order to obtain interference light L5, where the reflection light L4 is a portion of the signal light L3 which is reflected by a predetermined depth in a portion 12. The optical-path delay unit 300 is arranged in an optical path of the reference light L2, and varies the length of the optical path of the reference light L2. The optical scanning unit 400 scans with the signal light L3 the portion 12 of living tissue which is to be measured. The balance-difference detection unit 500 detects the intensity of the interference light L5 produced by interference between the reference light L2 and the reflection light L4. The signal processing unit 600 obtains the intensity of the reflection light L4 reflected by the predetermined surface of the portion 12, by heterodyne detection based on the intensity of the interference light L5 detected by the balance-difference detection unit 500, and converts the intensity of the reflection light L4 to an image signal. The image display unit 700 displays a tomographic image in accordance with the image signal obtained by the signal processing unit 600.

The light source unit 100 comprises a pulsed light source 110 and a pulse-width reduction unit 120. The pulsed light source 110 emits pulsed laser light having a wavelength of 780 nm. Hereinafter, the pulsed laser light may be called pulsed light. The pulse-width reduction unit 120 reduces the pulse width of the pulsed laser light emitted from the pulsed light source 110 by using chirped fiber Bragg gratings (chirped FBG), which is formed as an optical-waveguide structure.

The pulsed light source 110 comprises an erbium-doped fiber laser 111, a second-harmonic generator 112, and lenses 113 and 114. The erbium-doped fiber laser 111 is excited with excitation light having a wavelength of 980 nm, and emits pulsed laser light having a wavelength of 1.56 micrometers. The second-harmonic generator 112 generates a second harmonic of the pulsed laser light emitted from the erbium-doped fiber laser 111.

The pulse-width reduction unit 120 comprises a lens 137, optical circulators 121 to 124, chirped fiber Bragg grating (chirped FBGs) 125 to 128, and optical fibers 129 to 136. Each of the optical circulators 121 to 124 has three ports, and transmits pulsed laser light between the ports. The chirped FBGs 125 to 128 reduces the pulse width of the pulsed laser light. The chirped FBGs 125 to 128 are connected through the optical fibers 129 to 136 and the optical circulators 121 to 124.

Figure 2:
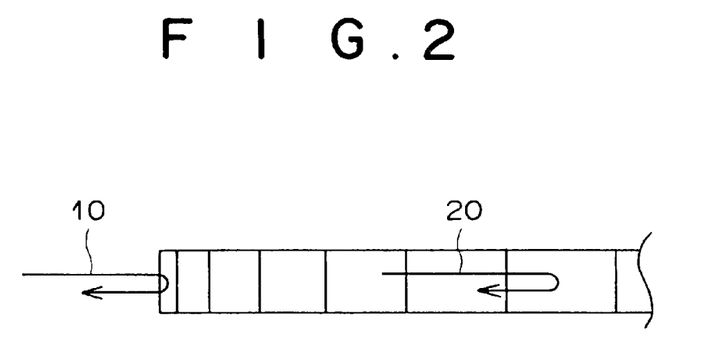
FIG. 2 is a side view of an example of a chirped fiber Bragg grating.

Each of the chirped FBGs 125 to 128 is a refractive-index-modulation type chirped FBG, in which a grating sectioned by high refractive index portions is formed as illustrated in FIG. 2.

Figure 3:
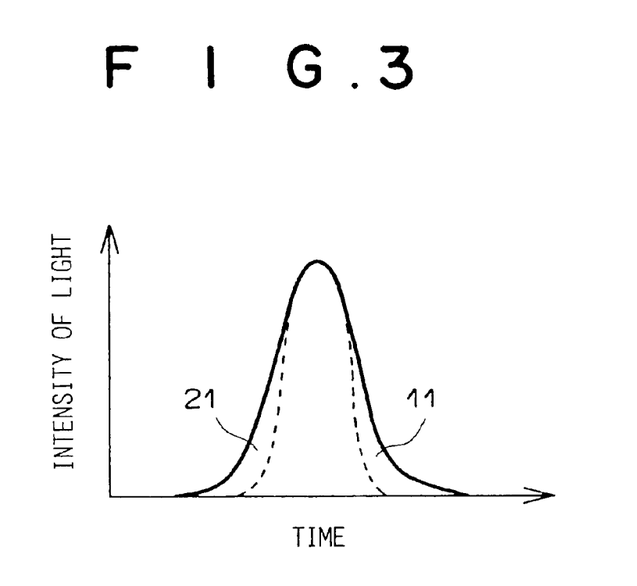
FIG. 3 is a diagram indicating examples of waveshapes of pulsed light before and after the pulse width is reduced.

Usually, fiber Bragg gratings (FBGs) are produced by arranging periodic high-refractive-index portions in an optical fiber by exposure to ultraviolet light so as to form a Bragg grating. Thus, the FBGs each behave as a reflection-type filter which reflects light having a wavelength corresponding to the pitch (period) of the Bragg grating. The pitches of the above Bragg gratings are constant. However, the pitch (period) of each chirped FBG progressively varies along the length of the chirped FBG. Therefore, a light component which enters the chirped FBG is reflected from a location in the chirped FBG corresponding to the wavelength of the light. That is, light components having different wavelengths are reflected from respectively different locations in the chirped FBG, as illustrated in FIG. 2. For example, a short-wavelength light component is reflected from a location at which the pitch is small, and a long-wavelength light component is reflected from a location at which the pitch is great. Therefore, the chirped FBG provides each light component with a delay corresponding to the wavelength of the light component. Generally, light components distribute in each laser light pulse in such a manner that light components 21 having longer wavelengths precede light components 11 having shorter wavelengths, as illustrated in FIG. 3. When such a laser light pulse enters the chirped FBG from the smaller pitch side, the pulse width of the laser light pulse can be reduced.

The pitch of each of the chirped FBGs 125 to 128 increases or decreases stepwise at regular intervals. The reflection wavelength band of the chirped FBG 125 corresponds to the pulse width of the pulsed laser light, and the reflection wavelength band of each of the chirped FBGs 126 to 128 corresponds to the pulse width of the pulsed laser light reduced by a chirped FBG in a preceding stage.

The chirped FBGs 125 to 128 are arranged so that laser light pulses enter each chirped FBG from the smaller pitch side. The chirped FBGs 125 to 128 are serially connected with the optical circulators 121 to 124 and the optical fibers 129 to 136. The output port of the optical circulator 124, which is located at the final stage in the pulse-width reduction unit 120, is connected to the fiber-coupling optical system 200.

The fiber-coupling optical system 200 comprises fiber couplers 201 and 202, a piezo electric element 203, and optical fibers 204 to 206. The fiber coupler 201 splits the low-coherence light L1 output from the light source unit 100, into signal light L3 and reference light L2, and multiplexes the reference light L2 and the reflection light L4 in order to obtain the interference light L5. The fiber coupler 202 is arranged between the light source unit 100 and the fiber coupler 201. The piezo electric element 203 causes a very small frequency shift in the reference light L2. The optical fibers 204 connects the light source unit 100 and the fiber coupler 202, the optical fiber 205 connects the optical-path delay unit 300 and an input of the fiber coupler balance-difference detection unit 500 through the fiber couplers 201 and 202, and the optical fiber 206 connects the optical scanning unit 400 and the other input of the balance-difference detection unit 500 through the fiber coupler 201. The optical fibers 204 to 206 are single-mode optical fibers.

The optical-path delay unit 300 comprises a lens 301 and a prism 302. The lens 301 collimates the reference light L2 output from the optical fiber 205, and returns the collimated reference light L2 to the optical fiber 205 after the collimated reference light L2 is reflected by the prism 302. The prism 302 reflects the collimated reference light L2, and changes the optical length of the reference light L2 when the prism 302 is moved in the direction of the optical path of the reference light L2 (i.e., in the horizontal direction in FIG. 1).

The optical scanning unit 400 comprises lenses 401 and 402 which move the signal light L3 in the direction perpendicular to the optical path of the signal light L3 (i.e., in the vertical direction in FIG. 1), and enters the reflection light L4 from the portion 12, into the optical fiber 206.

The balance-difference detection unit 500 comprises optical detectors 501 and 502 and a differential amplifier 503. The optical detectors 501 and 502 detect intensity of the interference light L5. The differential amplifier 503 adjusts the DC balance between the outputs of the optical detectors 501 and 502, cancels noise and drift components, and amplifies the difference between the outputs of the optical detectors 501 and 502.

Operations of First Embodiment

The operations of the optical coherence tomography apparatus of FIG. 1 are explained below.

In the pulsed light source 110, pulsed laser light being emitted from the erbium-doped fiber laser 111 and having a wavelength of 1.56 micrometers is converted to a second harmonic through the lens 113, the second-harmonic generator 112, and the lens 114. The second harmonic is pulsed laser light having a wavelength of 780 nm, and output to the pulse-width reduction unit 120.

In the pulse-width reduction unit 120, the above pulsed laser light is collected by the lens 137, and enters the optical fiber 129. The pulsed laser light propagates through the optical fiber 129, and enters the optical circulator 121 through an input port of the optical circulator 121. Then, the pulsed laser light is output through an input/output port of the optical circulator 121, propagates through the optical fiber 130, and enters the chirped FBG 125. The pulsed laser light is reflected by the chirped FBG 125, propagates through the optical fiber 130, and enters the optical circulator 121 through the input/output port of the optical circulator 121. When the pulsed laser light is reflected by the chirped FBG 125, the pulse width of the pulsed laser light is reduced. Then, the pulsed laser light is output through an output port of the optical circulator 121, propagates through the optical fiber 131, and enters the optical circulator 122 through an input port of the optical circulator 122. Thereafter, the pulsed laser light is reflected by the chirped FBGs 126, 127, and 128 in a similar manner to the above operation. When the pulsed laser light is reflected by the chirped FBGs 125, 126, 127, and 128, the pulse width of the pulsed laser light is reduced to about 5 fs while the center wavelength remains 780 nm. Finally, the pulsed laser light output from the chirped FBG 128 enters the optical fiber 204 through the optical circulator 124, and is supplied as low-coherence light L1 to the fiber-coupling optical system 200.

The low-coherence light L1 propagates through the optical fiber 204, is led to the optical fiber 205 through the fiber coupler 202, and split into the reference light L2 and the signal light L3. Next, the reference light L2 propagates through the optical fiber 205, is modulated by the piezo electric element 203, and is then led to the optical-path delay unit 300. Due to the modulation by the piezo electric element 203, the frequency of the reference light L2 is shifted from the frequency of the signal light L3 by a very small difference Δf. On the other hand, the signal light L3 propagates through the optical fiber 206 to the optical scanning unit 400.

In the optical scanning unit 400, the signal light L3 passes through the lenses 401 and 402, and enters the portion 12 of the living tissue which is to be measured. A portion of the signal light L3 which is reflected from a predetermined depth in the portion 12 is returned as the reflection light L4 to the optical fiber 206 through the lenses 402 and 401. In the fiber coupler 201, the reflection light L4 is optically multiplexed with the reference light L2 which is returned from the optical-path delay unit 300 through the optical fiber 205 as described below.

The reference light L2 which is modulated by the piezo electric element 203, and propagates through the optical fiber 205 to the optical-path delay unit 300 is collimated by the lens 301, and reflected by the prism 302. Then, the reflected reference light L2 passes through the lens 301, and is returned through the optical fiber 205 to the fiber coupler 201, in which the reflected reference light L2 is optically multiplexed with the reflection light L4, as described above.

Thus, the reference light L2 is superimposed on the reflection light L4 in the same optical path. When a predetermined condition exists, i.e., when the round trip optical length of the signal light L3 and the corresponding reflection light L4 between the fiber coupler 201 and the predetermined depth in the portion 12 coincides with the round trip optical length of the reference light L2 between the fiber coupler 201 and the prism 302 in the optical-path delay unit 300, interference occurs between the reflection light L4 and the reference light L2, and the interference light L5 containing a beat signal is generated.

Since the reference light L2 and the reflection light L4 are low-coherence light having a short coherence length, the interference occurs between the reflection light L4 and the reference light L2 when the round trip optical length of the signal light L3 and the corresponding reflection light L4 between the fiber coupler 201 and the predetermined depth in the portion 12 coincides with the round trip optical length of the reference light L2 between the fiber coupler 201 and the prism 302 in the optical-path delay unit 300. The frequency of the beat signal contained in the interference light L5 corresponds to the frequency difference $\Delta f$ between the reflection light L4 and the (frequency-shifted) reference light L2.

The interference light L5 is split into two portions by the fiber coupler 201. The first portion of the interference light L5 propagates through the optical fiber 205, and enters the optical detector 501, and the second portion of the interference light L5 propagates through the optical fiber 206, and enters the optical detector 502.

The optical detectors 501 and 502 respectively detect the intensities of the beat signal in the interference light L5. Then, the differential amplifier 503 obtains the difference between the outputs of the optical detectors 501 and 502, and outputs the difference to the signal processing unit 600. The differential amplifier 503 has a function of adjusting the DC balance between the two inputs thereof. Therefore, even when drift occurs in the low-coherence light L1 output from the light source unit 100, the drift components in the outputs of the optical detectors 501 and 502 can be canceled by adjusting the DC balance and amplifying the difference, and therefore only the beat signal component can be detected.

When the prism 302 is moved along the direction of the optical axis (i.e., the horizontal direction in FIG. 1), the optical length of the reference light L2 changes. Therefore, the total optical length of the reflection light L4 which interferes with the reference light L2 and the corresponding signal light L3 also changes with the change in the optical length of the reference light L2. Thus, the depth in the portion 12 from which the reflection light L4 interfering with the reference light L2 is reflected also changes. That is, the depth in the portion 12 from which the tomographic image is obtained can be changed by changing the position of the prism 302 in the direction of the optical axis.

As explained above, it is possible to obtain tomographic information along the optical axis of the optical scanning unit 400 from the surface of the portion 12 to a desired depth in the portion 12. Therefore, when the entire surface of the portion 12 is scanned by moving the incident point of the signal light L3 in a plane perpendicular to the optical axis of the optical scanning unit 400 (e.g., in the vertical direction in FIG. 1), and the above operation of obtaining tomographic information along the optical axis of the optical scanning unit 400 from the surface of the portion 12 to the desired depth in the portion 12 is repeated, tomographic information on the entire volume of the portion 12 can be obtained.

The signal processing unit 600 obtains the intensity of the reflection light L4 returned from a predetermined depth in the portion 12, by heterodyne detection based on the intensity of the interference light L5 detected by the balance-difference detection unit 500. Then, the signal processing unit 600 converts the intensity of the reflection light L4 into an image signal. Finally, the image display unit 700 displays a tomographic image in accordance with the image signal generated by the signal processing unit 600.

Advantages of First Embodiment

In the first embodiment of the present invention, the light source unit 100 is constituted by the pulsed light source 110 and the pulse-width reduction unit 120, and the pulsed light source 110 is constituted by the erbium-doped fiber laser 111 and the second-harmonic generator 112. In addition, the pulse-width reduction unit 120 reduces the pulse width of the low-coherence light by using the chirped FBGs 125 to 128, which are linear fiber Bragg gratings of the refractive-index modulation type. Therefore, the size and the cost of the light source unit 100 are reduced, and the usability of the light source unit 100 is increased.

In addition, the low-coherence light L1 emitted from the light source unit 100 has a center wavelength of 780 nm, a pulse width of about 5 fs, and a coherence length of 3 micrometers. That is, the resolution in the coherence interference is as high as 3 micrometers. Thus, the resolution in the coherence interference is so increased that a tomographic image of a microscopic structure of living tissue can be obtained, and this resolution is achieved by using only a small-sized, inexpensive, easy-to-handle light source, while the light sources required in the conventional optical coherence tomography apparatuses, such as the ultrashort-pulse laser, are expensive, bulky, and uneasy to handle.

Further, since the low-coherence light is in the 780 nm band, the low-coherence light exhibits desirable transmitting and scattering characteristics in the living tissue. Therefore, it is possible to obtain a desirable tomographic image.

Furthermore, since the pulsed light source 110 is constituted by the erbium-doped fiber laser 111 and the second-harmonic generator 112, pulsed laser light having a small pulse width and high output power can be obtained in a desirable wavelength band. In addition, since the pulse width of the pulsed laser light emitted from the light source unit 100 is 100 fs, the pulse width can be efficiently reduced to a desired amount.

Construction of Second Embodiment

Figure 4:
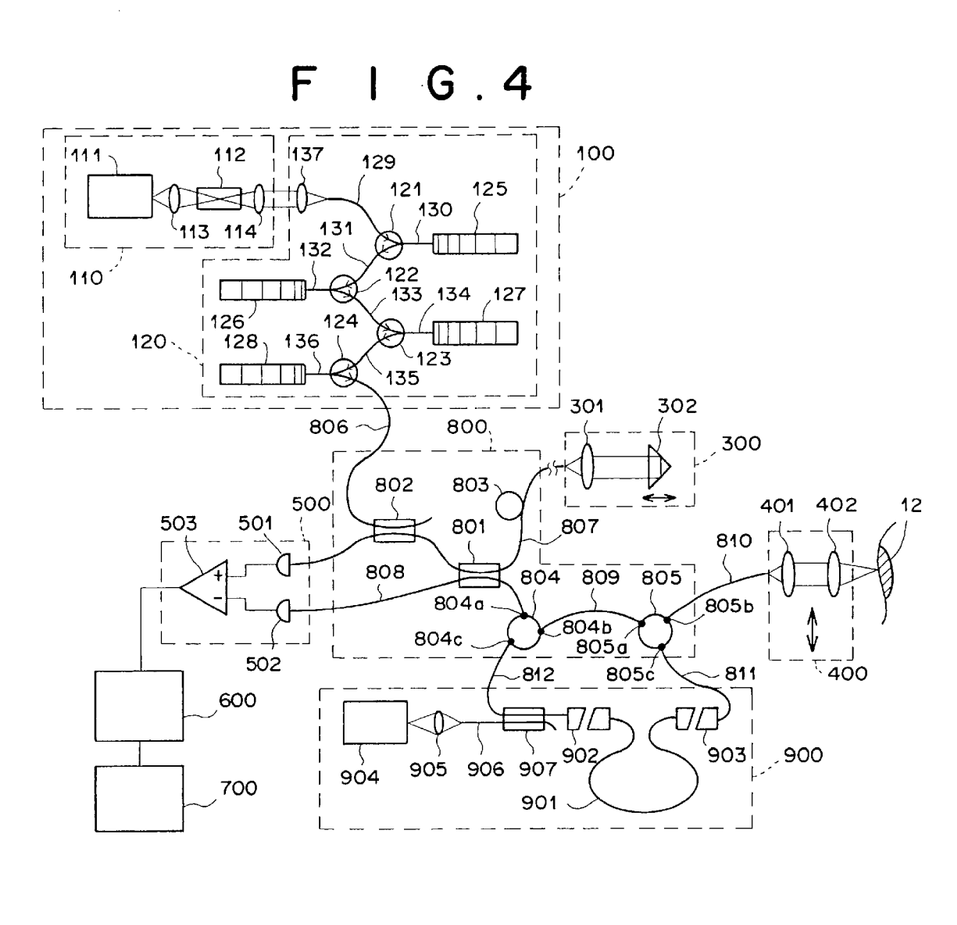
FIG. 4 is a diagram illustrating the construction of the second embodiment of the optical coherence tomography apparatus according to the present invention.

FIG. 4 is a diagram illustrating the construction of the second embodiment of the optical coherence tomography apparatus according to the present invention. The optical coherence tomography apparatus of FIG. 4 comprises a light source unit 100, a fiber-coupling optical system 800, an optical fiber amplifier unit 900, an optical-path delay unit 300, an optical scanning unit 400, a balance-difference detection unit 500, a signal processing unit 600, and an image display unit 700.

The light source unit 100 emits low-coherence light L1 having a center wavelength of 780 nm and a pulse width of about 100 fs. The fiber-coupling optical system 800 functions as an optical splitter and an optical multiplexer. The fiber-coupling optical system 800 splits the low-coherence light L1 emitted from the light source unit 100, into signal light L3 and reference light L2. The optical-path delay unit 300 is arranged in an optical path of the reference light L2, and varies the length of the optical path of the reference light L2. The optical fiber amplifier unit 900 amplifies reflection light L4, which is a portion of the signal light L3 which is reflected by a predetermined depth in a portion 12. The fiber-coupling optical system 800 optically multiplexes the amplified reflection light L4' and the reference light L2 in order to obtain interference light L5'. The optical scanning unit 400 scans with the signal light L3 the portion 12 of living tissue which is to be measured. The balance-difference detection unit 500 detects the intensity of the interference light L5' produced by interference between the reference light L2 and the amplified reflection light L4'. The signal processing unit 600 obtains the intensity of the amplified reflection light L4' by heterodyne detection based on the intensity of the interference light L5' detected by the balance-difference detection unit 500, and converts the intensity of the amplified reflection light L4' to an image signal. The image display unit 700 displays a tomographic image in accordance with the image signal obtained by the signal processing unit 600. The light source unit 100, the optical-path delay unit 300, the optical scanning unit 400, the balance-difference detection unit 500, the signal processing unit 600, and the image display unit 700 have the same constructions and functions as the corresponding units in the construction of FIG. 1, respectively.

The fiber-coupling optical system 800 comprises fiber couplers 801 and 802, a piezo electric element 803, optical circulators 804 and 805, and optical fibers 806 to 812. The fiber coupler 801 splits the low-coherence light L1 output from the light source unit 100, into signal light L3 and reference light L2, and optically multiplexes the reference light L2 and the amplified reflection light L4' in order to obtain interference light L5'. The fiber coupler 802 is arranged between the light source unit 100 and the fiber coupler 801. The optical circulator 804 has three ports 804a, 804b, and 804c, and transmits the reference light L2 and the amplified reflection light L4' between the ports. The optical circulator 805 also has three ports 805a, 805b, and 805c, and transmits the reference light L2 and the reflection light L4 between the ports. The piezo electric element 803 shifts the frequency of the reference light L2 by a very small amount. The optical fibers 806 connects the light source unit 100 and the fiber coupler 802, the optical fiber 807 connects the optical-path delay unit 300 and an input of the fiber coupler balance-difference detection unit 500 through the fiber couplers 801 and 802. The optical fiber 808 connects the optical circulator 804 and the other input of the balance-difference detection unit 500 through the fiber coupler 801. The optical fiber 809 connects the optical circulators 804 and 805. The optical fiber 810 connects the optical circulator 805 and the optical scanning unit 400. The optical fiber 811 connects the optical circulator 805 and an optical connector 903 in the optical fiber amplifier unit 900 (explained later). The optical fiber 812 connects the optical circulator 804 and an optical connector 902 in the optical fiber amplifier unit 900. The optical fibers 806 to 812 are single-mode optical fibers.

The optical fiber amplifier unit 900 comprises a fiber amplification portion 901, the optical connectors 902 and 903, a YAG laser 904, a lens 905, an optical fiber 906, and the fiber coupler 907. The fiber amplification portion 901 is arranged between the optical connectors 902 and 903, and amplifies signal light propagating through the fiber amplification portion 901 when the fiber amplification portion 901 is excited. The YAG laser 904 generates as excitation light L6 a second harmonic having a wavelength of 532 nm, and supplies the excitation light L6 to the optical fiber 906 through the lens 905. The lens 905 collects the excitation light L6 output from the YAG laser 904. The optical fiber 906 leads the collected excitation light L6 to the fiber coupler 907. The fiber coupler 907 leads the excitation light L6 to the optical fiber 812. The fiber amplification portion 901 is realized by an optical fiber including a core doped with $Ti^{4+}$, which has a peak gain in the vicinity of 780 nm. The optical fiber is wound when placed in the optical fiber amplifier unit 900.

Operations of Second Embodiment

The operations of the optical coherence tomography apparatus of FIG. 4 are explained below.

The low-coherence light L1 having a wavelength of 780 nm is output from the light source unit 100, and enters the optical fiber 806. The low-coherence light L1 propagates through the optical fiber 806, and is led through the fiber coupler 802 to the optical fiber 807. Then, the low-coherence light L1 propagates through the optical fiber 807 to the fiber coupler 802, by which the low-coherence light L1 is split into the reference light L2 and the signal light L3. The reference light L2 propagates through the optical fiber 807, and is modulated by the piezo electric element 803 so that the frequency of the reference light L2 is shifted by a very small amount. Thus, a very small frequency difference is produced between the reference light L2 and the signal light L3. On the other hand, the signal light L3 propagates through the optical fiber 808, enters the optical circulator 804 through the port 804a, and is then output from the port 804b to the optical fiber 809. Next, the signal light L3 propagates through the optical fiber 809, enters the optical circulator 805 through the port 805a, and is then output from the port 805b to the optical fiber 810. The signal light L3 further propagates through the optical fiber 810 to the optical scanning unit 400.

In the optical scanning unit 400, the signal light L3 passes through the lenses 401 and 402, and enters the portion 12 of the living tissue which is to be measured. A portion of the signal light L3 which is reflected from a predetermined depth in the portion 12 is returned as the reflection light L4 to the optical fiber 810 through the lenses 402 and 401. The reflection light L4 propagates through the optical fiber 810, enters the optical circulator 805 through the port 805b, and is output from the port 805c to the optical fiber 811. Thus, the reflection light L4 enters the optical fiber amplifier unit 900, and is amplified by the optical fiber amplifier unit 900. Details of the operations of the optical fiber amplifier unit 900 are explained later. The amplified reflection light L4' propagates through the optical fiber 812, the optical circulator 804, and the optical fiber 808 to the fiber coupler 801.

On the other hand, the reference light L2 modulated by the piezo electric element 803 propagates through the optical fiber 807 to the optical-path delay unit 300. In the optical-path delay unit 300, the reference light L2 is collimated by the lens 301, and reflected by the prism 302. Then, the reflected reference light L2 passes through the lens 301, is returned to the optical fiber 807, and then propagates to the fiber coupler 801.

Thus, the reference light L2 is superimposed on the amplified reflection light L4' in the same optical path. When a predetermined condition exists, i.e., when the total optical length of the signal light L3, the corresponding reflection light L4, and the corresponding amplified reflection light L4' between the fiber coupler 801 and the predetermined depth in the portion 12 coincides with the round trip optical length of the reference light L2 between the fiber coupler 801 and the prism 302 in the optical-path delay unit 300, interference occurs between the amplified reflection light L4' and the reference light L2, and the interference light L5' containing a beat signal is generated.

The interference light L5' is split into two portions by the fiber coupler 801. The first portion of the interference light L5' propagates through the optical fiber 807, and enters the optical detector 501, and the second portion of the interference light L5' propagates through the optical fiber 808, and enters the optical detector 502.

The optical detectors 501 and 502 respectively detect the intensities of the beat signal in the interference light L5'. Then, the differential amplifier 503 obtains the difference between the outputs of the optical detectors 501 and 502, and outputs the difference to the signal processing unit 600. The signal processing unit 600 obtains the intensity of the amplified reflection signal light L4' by heterodyne detection based on the intensity of the interference light L5' detected by the balance-difference detection unit 500. Then, the signal processing unit 600 converts the intensity of the amplified reflection signal light L4' into an image signal. Finally, the image display unit 700 displays a tomographic image in accordance with the image signal generated by the signal processing unit 600.

When the prism 302 is moved along the direction of the optical axis (i.e., the horizontal direction in FIG. 1), the optical length of the reference light L2 changes. Therefore, the total optical length of the amplified reflection light L4' which interferes with the reference light L2, the corresponding signal light L3, and the corresponding reflection light L4 also changes with the change in the round trip optical length of the reference light L2. Thus, the depth in the portion 12 from which the reflection light L4 corresponding to the amplified reflection light L4' interfering with the reference light L2 is reflected also changes. That is, the depth in the portion 12 from which the tomographic image is obtained can be changed by changing the position of the prism 302 in the direction of the optical axis.

As explained above, it is possible to obtain tomographic information along the optical axis of the optical scanning unit 400 from the surface of the portion 12 to a desired depth in the portion 12. Therefore, when the entire surface of the portion 12 is scanned by moving the incident point of the signal light L3 in a plane perpendicular to the optical axis of the optical scanning unit 400 (e.g., in the vertical direction in FIG. 1), and the above operation of obtaining tomographic information along the optical axis of the optical scanning unit 400 from the surface of the portion 12 to the desired depth in the portion 12 is repeated, tomographic information on the entire volume of the portion 12 can be obtained.

The operations of the optical fiber amplifier unit 900 are explained below.

The excitation light L6 emitted by the YAG laser 904 having the wavelength of 532 nm is collected by the lens 905, and enters the optical fiber 906. Then, the excitation light L6 is led to the optical fiber 812 through the fiber coupler 907, and enters the fiber amplification portion 901 through the optical connector 902. During propagation of the excitation light L6 through the fiber amplification portion 901, the excitation light L6 is absorbed by $Ti^{4+}$ with which the core of the fiber amplification portion 901 is doped. When $Ti^{4+}$ absorbs the excitation light L6, $Ti^{4+}$ transits from its ground state to an excited state. When the reflection light L4 enters the fiber amplification portion 901 in which $Ti^{4+}$ is excited, through the optical connector 903, and propagates through the fiber amplification portion 901, light in phase with the reflection light L4 is generated by induced emission, and $Ti^{4+}$ returns to the ground state. The induced emission repeatedly occurs, and amplifies the reflection light L4. Thus, the amplified reflection light L4' is emitted through the optical connector 902. Since the amplified reflection light L4' is in phase with the reflection light L4, the tomographic information can be obtained from the interference light L5' generated by the interference between the reference light L2 and the amplified reflection light L4'.

Advantages of Second Embodiment

The optical coherence tomography apparatus as the second embodiment of the present invention has the following advantages as well as the advantages of the first embodiment.

Since the optical fiber amplifier unit 900 is provided, and the reflection light L4 is amplified before the interference with the reference light L2, it is possible to obtain tomographic information having an enhanced signal-to-noise ratio while keeping the intensity of the signal light L3 at such a level that the safety of the portion 12 of the living tissue is secured. In addition, even when the reflection light L4 is returned from a deep area from which the conventional optical coherence tomography apparatuses cannot obtain tomographic information, the interference light L5' generated by the interference between the reference light L2 and the amplified reflection light L4' can be detected, and therefore the tomographic information can be obtained. That is, the depth from which tomographic information can be obtained is increased by the provision of the optical fiber amplifier unit 900.

In addition, since the optical fiber as the fiber amplification portion 901 can be wound for compact placement, it is possible to increase the length of the optical fiber to a length which realizes a desired gain without substantially increasing the size of the optical fiber amplifier unit 900. That is, the reflection light L4 can be amplified with a great gain by using a small-sized optical fiber amplifier unit 900. Since optical fiber amplifiers have low-noise characteristics, it is possible to accurately amplify very weak reflection light L4.

Further, since an optical fiber doped with $Ti^{4+}$ is used in the fiber amplification portion 901, it is possible to efficiently amplify the reflection light L4 in the wavelength band near 780 nm.

Since the wavelength of the low-coherence light L1, i.e., the wavelength of the signal light L3, is 780 nm, the reference light L2 exhibits desirable transmitting and scattering characteristics in the living tissue. Therefore, it is possible to obtain a desirable tomographic image.

Variations and Other Matters (i) As a variation of each of the first and second embodiments of the present invention, a pulsed light source which emits pulsed laser light having a wavelength of 1,560 nm, instead of 780 nm, can be used. That is, the erbium-doped fiber laser 111 can be singly used as the pulsed light source 110. In this case, an optical fiber doped with $Er^{3+}$, instead of $Ti^{4+}$, can be used in the optical fiber amplifier unit 900, and a semiconductor laser which emits laser light having a wavelength of 980 nm, instead of the YAG laser 904 emitting the laser light of 532 nm, can be used as an excitation light source in the optical fiber amplifier unit 900. In the above variation, the excitation light L6 having the wavelength of 980 nm is absorbed by $Er^{3+}$ in the fiber amplification portion 901, and reflection light L4 having the wavelength of 1,560 nm can be efficiently amplified in the fiber amplification portion 901.

(ii) In addition, according to the wavelength band of the low-coherence light L1, at least one ion from among transition-metal ions, rare-earth ions, and complex ions can be used as a dopant in the optical fiber in the optical fiber amplifier unit 900. When at least one ion from among the transition-metal ions $Ti^{4+}$, $Cr^{3+}$, $Mn^{4+}$, $Mn^{2+}$, and $Fe^{3+}$, rare-earth ions $Sc^{3+}$, $Y^{3+}$, $La^{3+}$, $Ce^{3+}$, $Pr^{3+}$, $Nd^{3+}$, $Pm^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, and $Lu^{3+}$, and complex ions $WO_4^{2-}$, $MoO_4^{2-}$, $VO_4^{3+}$, $Pt(CN)_4^{2-}$, and $WO_6^{6-}$ is used as a dopant in the optical fiber as the optical fiber amplifier unit 900, the reflection light L4 can be efficiently amplified. In addition, since optical fibers can be easily doped with the above ions, the manufacturing cost of the fiber amplification portion 901 can be reduced. Alternatively, a dye-doped optical fiber can be used as the fiber amplification portion 901.

(iii) Although four chirped FBGs are used in the pulse-width reduction unit 120 in the optical coherence tomography apparatuses of FIGS. 1 and 4, any number of chirped FBGs can be used when that number of chirped FBGs can reduce the pulse width of the pulsed laser light emitted from the pulsed light source 110 to a desired pulse width. For example, the number may be one, two, three, five, or more.

(iv) Instead of the chirped FBGs, transparent-type finely-structured optical waveguides each of which contains microbubbles, such as air foam, in the core can be used. In the transparent-type finely-structured optical waveguides, the zero-dispersion wavelength is shifted toward the shorter-wavelength side by forming microbubbles in the core so as to change the structure dispersion characteristic of the optical fiber. Therefore, an anomalous dispersion characteristic can be obtained in a desired wavelength band. Thus, when pulsed laser light propagates through a transparent-type finely-structured optical waveguide formed as above, the pulse width of the pulsed laser light is reduced. In this case, the reduction of the pulse width can be realized by merely transmitting the pulsed laser light through the finely-structured optical waveguide. Therefore, the construction of the pulse-width reduction unit 120 can be simplified, and the size of the pulse-width reduction unit 120 can be reduced.

(v) Although the pulsed light source 110 in the optical coherence tomography apparatuses of FIGS. 1 and 4 comprises the erbium-doped fiber laser 111 and the second-harmonic generator 112, the construction of the pulsed light source 110 is not limited to the pulsed light source 110 illustrated in FIGS. 1 and 4. For example, according to the required conditions concerning the wavelength band, the output power, the pulse width, and the like, the pulsed light source 110 may be realized by singly using an erbium-doped fiber laser or a fiber laser doped with another rare-earth element such as ytterbium, or using an fiber laser doped with another rare-earth element such as ytterbium and a second-harmonic generator in combination. In addition, the titanium sapphire laser or the like is suitable for use in a pulsed light source.

(vi) In the optical coherence tomography apparatuses as the first and second embodiments, the piezo electric element is arranged in the optical path of the reference light in order to shift the frequency of the reference light. As an alternative, instead of shifting the frequency of the reference light, the frequency of the signal light may be shifted. As a second alternative, both of the frequencies of the reference light and the signal light can be shifted so as to produce a desired difference between the frequencies of the reference light and the signal light.

What is claimed is:

1. An optical coherence tomography apparatus comprising:
   a light source which emits low-coherence light;
   an optical splitting unit which splits said low-coherence light into signal light having a first frequency and first reference light having a second frequency;
   a frequency shifting unit which shifts at least one of said first and second frequencies so that a predetermined frequency difference is produced between the first and second frequencies;
   an irradiating unit which irradiates an object with said signal light;
   an optical multiplexing unit which optically multiplexes said reference light and a portion of said signal light which is reflected from a predetermined depth in said object, so as to produce interference light; and
   an image detection unit which detects an optical intensity of said interference light, and obtains a tomographic image of said object based on said optical intensity;
   said light source comprises,
      a pulsed light source unit which emits pulsed light having a third frequency and a pulse width, and
      an optical-waveguide structure made of a material having a normal dispersion characteristic with respect to light which has said third frequency, where said optical-waveguide structure includes a structure which realizes an anomalous dispersion characteristic with respect to light which has said third frequency, so as to reduce said pulse width of said pulsed light.

2. An optical coherence tomography apparatus according to claim 1, wherein said optical-waveguide structure comprises at least one Bragg grating formed with a plurality of light-reflecting portions arranged in a longitudinal direction of said optical-waveguide structure at a pitch which varies progressively.

3. An optical coherence tomography apparatus according to claim 2, wherein said at least one Bragg grating is at least one frequency-modulation type Bragg grating formed with a plurality of high-refractive-index portions arranged in the longitudinal direction of said optical-waveguide structure at said pitch.

4. An optical coherence tomography apparatus according to claim 2, wherein said at least one Bragg grating is at least one linear Bragg grating in which said pitch varies linearly.

5. An optical coherence tomography apparatus according to claim 1, wherein said at least one Bragg grating is at least one chirped fiber Bragg grating.

6. An optical coherence tomography apparatus according to claim 1, wherein said pulsed light source comprises a fiber laser doped with a rare-earth ion.

7. An optical coherence tomography apparatus according to claim 1, wherein said pulsed light source further comprises a second harmonic generator.

8. An optical coherence tomography apparatus according to claim 6, wherein said rare-earth ion is erbium.

9. An optical coherence tomography apparatus according to claim 6, wherein said rare-earth ion is ytterbium.

10. An optical coherence tomography apparatus according to claim 1, wherein said pulsed light source comprises a titanium sapphire laser.

11. An optical coherence tomography apparatus according to claim 1, wherein said pulse width of said pulsed light is in a range from 10 fs to 1 ps.

12. An optical coherence tomography apparatus according to claim 1, further comprising an optical amplifying unit which optically amplifies said a portion of said signal light before optically multiplexed with said reference light.

13. An optical coherence tomography apparatus according to claim 12, wherein said optical amplifying unit is an optical amplifier comprising an optical waveguide.

14. An optical coherence tomography apparatus according to claim 13, wherein said optical amplifier is an optical fiber amplifier.

15. An optical coherence tomography apparatus according to claim 14, wherein said optical fiber amplifier comprises an optical fiber doped with at least one ion from among transition-metal ions, rare-earth ions, and complex ions.

16. An optical coherence tomography apparatus according to claim 15, wherein said optical fiber is doped with at least one ion from among transition-metal ions $Ti^{4+}$, $Cr^{3+}$, $Mn^{4+}$, $Mn^{3+}$, and $Fe^{3+}$, rare-earth ions $Sc^{3+}$, $Y^{3+}$, $La^{3+}$, $Ce^{3+}$, $Pr^{3+}$, $Nd^{3+}$, $Pm^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, and $Lu^{3+}$, and complex ions $WO_4^{2-}$, $MoO_4^{2-}$, $VO_4^{3+}$, $Pt(CN)_4^{2-}$, and $WO_6^{6-}$.

17. An optical coherence tomography apparatus according to claim 14, wherein said optical fiber amplifier comprises a dye-doped optical fiber.

18. An optical coherence tomography apparatus according to claim 1, wherein said object is a portion of living tissue, and said low-coherence light has a wavelength in a range from 600 nm to 1,700 nm.

* * * * *